United States Patent [19]

Burke

[11] Patent Number: 4,803,994

[45] Date of Patent: Feb. 14, 1989

[54] BACKSCATTER DATA COLLECTION TECHNIQUE FOR ULTRASOUND

[75] Inventor: Thomas M. Burke, Rancho Cordova, Calif.

[73] Assignee: General Electric Company, Milwaukee, Wis.

[21] Appl. No.: 84,228

[22] Filed: Aug. 12, 1987

[51] Int. Cl.$^4$ ............................................. A61B 10/00
[52] U.S. Cl. .................................................. 128/660.06
[58] Field of Search ....................... 128/660, 661, 663; 73/602

[56] References Cited

U.S. PATENT DOCUMENTS

| | | | |
|---|---|---|---|
| 4,320,765 | 3/1982 | Cathignol et al. | 128/663 |
| 4,470,303 | 9/1984 | O'Donnell | 73/602 |
| 4,534,359 | 8/1985 | Miller-Jones et al. | 128/660 |
| 4,564,019 | 1/1986 | Miwa | 128/660 |
| 4,662,222 | 5/1987 | Johnson | 73/602 |
| 4,688,428 | 8/1987 | Nicolas | 73/602 |

OTHER PUBLICATIONS

Namery, J. et al., "UTS Detection of MI in Dog", IEEE Ultrasonics 1972, pp. 491–494.
Shung, K. K. et al., "Scattering of UTS by Blood," IEEE BME Trans., vol. 23, #6, pp. 460–467, Nov. 1976.
Perez, J. E. et al., "Applicability of UTS Tissue Characterization in Cardiomyopathy", JACC, vol. 4, #1, Jul. 1984, pp. 88–95.
Sommer et al., "Tissue Characterization Via Envelope Amplitude Analysis Following Narrowband Filtering of the Ultrasonic System", Ultrasonic Imaging, 1986, vol. 8, No. 1, p. 64.
"Waveform Analysis Improves Tissue Differentiation," Diagnostic Imaging, Jun. 1987, p. 31.
Nicholas, "The Application of Acoustic Scattering Parameters to the Characterisation of Human Soft Tissue," IEEE Ultrasonics Symposium Proceedings (1976), pp. 64–69.
Lizzi et al., "Clinical Spectrum Analysis Techniques for Tissue Characterization," Ultrasonic Tissue Characterization II, National Bureau of Standards, Spec. Publ. 525, 1979, pp. 111–119.
Nicholas, "Evaluation of Backscattering Coefficients for Excised Human Tissues," Ultrasound in Medicine & Biology 1982, vol. 8, No. 1, pp. 17–28.
Fei et al., "Ultrasonic Backscatter from Bovine Tissues," J. Acoust. Soc. Am. 81(1), Jan. 1987, pp. 166–172.

Primary Examiner—Francis J. Jaworski
Attorney, Agent, or Firm—Mark L. Mollon; Douglas E. Stoner

[57] ABSTRACT

A rapid, non-invasive realtime modality for detecting differential backscatter in ultrasound is achieved using narrowband interrogating frequencies to maximize signal-to-noise ratio and to minimize location errors. Additional improvement in signal-to-noise ratio and separation of tissue populations are achieved by cyclically alternating through a fixed number of predetermined burst lengths and by employing multiple narrowband bursts of differing fundamental frequencies.

13 Claims, 1 Drawing Sheet

BACKSCATTER DATA COLLECTION TECHNIQUE FOR ULTRASOUND

BACKGROUND OF THE INVENTION

The present invention relates in general to ultrasound apparatus for medical diagnostic imaging, and more specifically to measurement and display of differential backscatter cross section per unit volume of insonified tissue.

Acoustic parameters useful in medical ultrasound include reflection at discontinuities, volume backscatter coefficient, absorption coefficient and Doppler frequency shift. Ultrasonic measurement of these parameters provides a basis for various tissue characterizations and for constructing images. Although reflection imaging (using extrinsic measurements) has historically been the principal basis for diagnostic ultrasound, it is realized that intrinsic parameters are useful for tissue localization and characterization and for detection of pathology.

Backscatter coefficient has been investigated for its utility in imaging and characterization and has been found to provide diagnostically useful quantitative data. However, tissue pathology is not alwasy readily apparent from absolute measurements of the backscatter coefficient. For example, it is sometimes required to perform filtering of broadband backscatter data to find frequency dependencies of the backscatter coefficient to identify pathological tissue.

The success of a diagnostic modality in providing useful information depends on an ability to interrogate tissue and acquire acoustic data with a maximum signal-to-noise ratio (SNR). However, specular reflections, signal correlations, inhomogeneous attenuation, and other factors result in a generally low SNR in ultrasound backscatter measurement.

Accordingly, it is a principal object of the present invention to provide a method and apparatus for collecting quantitative backscatter data.

It is another object to improve tissue characterization and diagnosis by means of quantitative backscatter data.

It is another object to improve the signal-to-noise ratio in measurements of intrinsic acoustic parameters for ultrasound.

It is still another object of the invention to detect localized variations in backscatter intensity and dependencies in an object.

SUMMARY OF THE INVENTION

These and other objects are achieved in an ultrasound system for measuring differential backscatter across a selected volume of tissue or organ and for detecting temporal and frequency dependencies of backscatter in order to distinguish between normal and diseased tissue.

By way of example, sufficient contrast exists between backscatter measurements of normal and diseased myocardial tissues to allow detection and imaging by ultrasound. Infarcted tissue exhibits increased backscatter where the local amount of collagen is increased and also exhibits increased signal attenuation related to local collagen concentration and depletion of creatine kinase, relative to normal myocardial tissues. Severely ischemic myocardium (e.g., 80 percent reduction of local blood flow) results in about a 5 dB increase in backscatter but in a decrease in attenuation. Furthermore, the cyclic variation present in the backscatter intensity of normal myocardium which has a minimum near occurrence of end systole and has a maximum near occurrence of end diastole appears weakened in ischemic tissue. Thus, imaging of the differential backscatter cross section per unit volume of insonified tissue of a heart and its temporal and/or frequency dependence resulting from various tissue populations enables detection of various pathological areas.

The signal-to-noise ratio of backscatter measurements in the present invention is improved by employing narrowband interrogating signals to reduce statistical variations in backscatter intensity and to improve tissue regionalization. Use of narrowband signals also eliminates the need for range gating in signal processing. SNR is further improved by obtaining and combining substantially uncorrelated measurements of a target volume without moving the vector angle by repetitively firing narrowband bursts of varying length or cycles.

In another aspect of the invention, measurements are obtained using a plurality of sequential narrowband interrogating bursts of different fundamental frequencies to characterize tissue in terms of a combination of scatter contribution from cellular and parenchymal tissue architectures as a further means of tissue discrimination. Thus, frequency dependencies of the backscatter coefficient are employed to infer contrasts in tissue structure according to an empirically derived model.

BRIEF DESCRIPTION OF THE DRAWINGS

The novel features of the invention are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
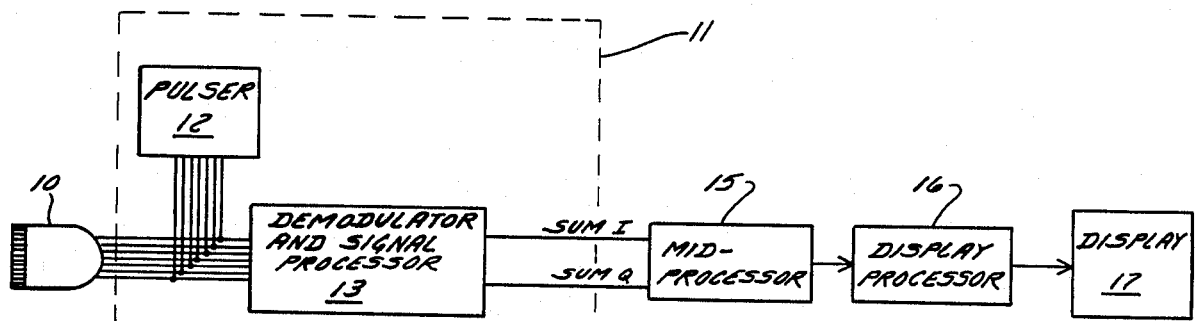
FIG. 1 is a block diagram of an ultrasonic system for practicing the present invention.

Referring now to FIG. 1 a receive/transmit transducer 10 comprising a plurality of transducer elements in an array is coupled to a front-end processor 11 which includes a pulser 12 and a demodulator and signal processor 13. The ultrasound system further includes a mid-processor 15, display processor 16 and a display 17. Pulser 12 energizes transducer array 10 to insonify along a vector angle in an object. In a receive mode, signals detected by transducer array 10 are coupled to demodulator and signal processor 13 which operates in a known manner to provide a summed in-phase signal I and summed quadrature signal Q which are phase insensitive.

Mid-processor 15 determines the backscatter intensity based on signals I and Q. The intensity or other backscatter feature is provided to a display processor 16 for presentation on display 17 in any desired format. Other backscatter parameters having diagnostic utility include temporal changes in backscatter intensity (e.g., difference between systole and diastole for cardiac tissue) which can be measured and displayed. Another example is the frequency dependence of the backscatter coefficient which is used to detect variation in tissue structure, as will be described later.

In a preferred embodiment of the invention, tissue features such as lesions can be detected in a target organ by separating various tissue populations according to localized differential backscatter coefficient. The backscatter coefficient at each resolved point, taken at one or more frequencies, provides the data used to detect lesions and provide secondary information to confirm diagnoses or locate a lesion for follow-up exams or treatment, for example.

Figure 2:
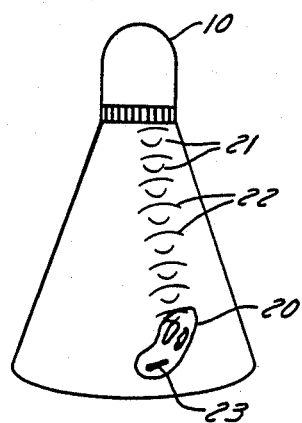
FIG. 2 shows the acquisition of an ultrasonic image.

Ultrasonic interrogation of an organ is represented in FIG. 2. Transducer 10 transmits ultrasonic energy toward a heart 20. Transmitted ultrasonic waves 21 interact with heart 20 to produce backscattered waves 22. In one preferred embodiment of the present invention, a typical B-mode image of heart 20 is presented on display 17. Thereafter, localized differential backscatter information is collected for the same image area and is overlaid on the B-mode image (by adding various colors, for example) so that a lesion 23 can be detected in heart 20. Alternatively, a two-dimensional (2D) B-mode image corresponding only to localized backscatter coefficients can be employed.

In biological tissue, the actual scatterers that cause backscatter and their separation are not known. If a small tissue volume of scatterers (such as 1 cc) is investigated, independent measurements of backscatter cross section (i.e., backscatter intensity) of the tissue sample are subject to large statistical variations because of tissue structures. This variation in independent measurements of a single target area makes it difficult or impossible to separate tissue populations based on backscatter intensity. According to the present invention, it is found that use of a narrowband frequency for the transmitted ultrasonic energy will select a larger scatterer volume to give consistent intensity measurements and better signal-to-noise performance.

The improved signal-to-noise performance of the present narrowband systems results from a reduction in backscatter intensity variations because of the larger volume of scatterers (scatter number) associated with each backscatter pixel (i.e., target volume). Mean number of scatterers per unit volume follows a Poisson distribution, such that the variation in backscatter intensity varies as the square root of the mean number of scatterers in the effective scatterer volume. Thus, an effective scatterer volume containing 10 scatters provides standard deviation in intensity measurements of about 30 percent. An increased effective scatterer volume containing 100 scatterers improves intensity standard deviation to 10 percent. Therefore, signal-to-noise and the ability to separate tissue populations are improved according to the narrowband system of the present invention.

The narrowband transmission of the present invention has the further advantage of improved lateral and depth regionalization by reducing frequency dependencies and interactions present with a wideband system. The wideband effects caused by interference between component frequencies are avoided in the present invention.

Figure 3:
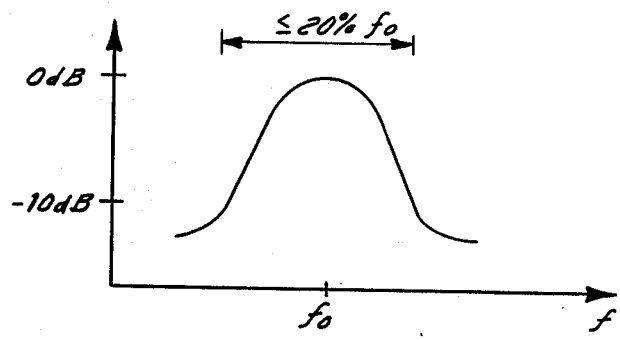
FIG. 3 illustrates the transmission bandwidth employed in the present invention.

Turning now to FIG. 3, an exemplary frequency spectrum for the narrowband transmission of the present invention is shown. A narrowband signal is centered on a fundamental frequency $f_o$. The ability to define a narrowband energy transmission depends on the passband characteristics of the pulsing system and the number of cycles of the fundamental frequency in an interrogating burst. In the present invention, the bandwidth is sufficiently narrow so that all of the backscattered energy can be considered as coming from the fundamental frequency. As shown in FIG. 3, a $-10$ dB fractional bandwidth less than about 20 percent is employed. Further, a preferred fractional bandwidth of between 10 and 20 percent provides excellent narrowband results.

A further improvement in the SNR received for each target volume is achieved by the present invention by repetitively firing narrowband bursts of varying length to acquire backscattered data for each target volume. For example, narrowband performance occurs in a system employing a fundamental frequency in the range of several megahertz when interrogating bursts of 3 or more cycles are used. A first interrogating burst of 3 cycles can be averaged with a subsequent burst length of 5 cycles at the same target volume. The varied burst length alters the receive amplitude statistics, such that a substantially independent estimate of the backscatter intensity is obtained without moving the interrogating vector angle. Each independent measurement is partially uncorrelated so as to improve the SNR of the signal average. The change in burst length or cycles slightly alters the spectral content of the interrogating beam, as well as changes the volume of scatterer that contribute to the signal. In a preferred embodiment, separate interrogating bursts of 7, 9 and 11 cycles are employed at a fundamental frequency of 2.5 MHz to obtain three partially uncorrelated measurements which are equivalent to about 2.5 independent samples of the target volume. At a fundamental frequency of 3.6 MHz, burst lengths of 10, 13, and 16 cycles have been employed with good results.

In another aspect of the invention, backscatter intensity measurements that provide independent, uncorrelated estimates are obtained at a plurality of fundamental frequencies in separate, sequential measurements using narrowband transmission. Thus, one or more interrogations are performed at a first fundamental frequency and may include bursts of varying cycles. Other measurements obtained at a second fundamental frequency are combined with the measurements at the first fundamental frequency to generate a value for the backscatter intensity.

Backscatter measurements at a plurality of narrowband frequencies are further employed in the invention to find the frequency dependence of backscatter for a target area of tissue. This frequency dependence enables characterization of tissue in terms of the relative backscatter contribution from cellular and parenchymal scatterer populations. Backscatter coefficient N as a function of a frequency f can be modeled according to the equation:

$$N(f) = W_1 f + W_2 f^4$$

where $W_1$ and $W_2$ are empirically derived factors thought to represent Mie region scattering objects and Rayleigh-like scattering objects within tissue, respectively.

When N(f) is measured at two frequencies (e.g., 2.5 MHz and 3.6 MHz), two equations are obtained and solutions for $W_1$ and $W_2$ can be found using matrix mathematics. For the case with $f_1 = 2.5$ MHz and $f_2 = 3.6$ MHz, the solutions are:

$W_1 = N(2.5 \text{ MHz})D - N(3.6 \text{ MHz})B$ and $W_2 = N(3.6 \text{ MHz})A - N(2.5 \text{ MHz})C$ where A=2.5, B=3.6, C=39, and D=168.

The two main tissue populations (i.e., cellular and parenchymal) are thus distinguishable by the determination of $W_1$ and $W_2$, and images corresponding to values of $W_1$ and/or $W_2$ provide a representation of tissue architecture.

Figure 4:
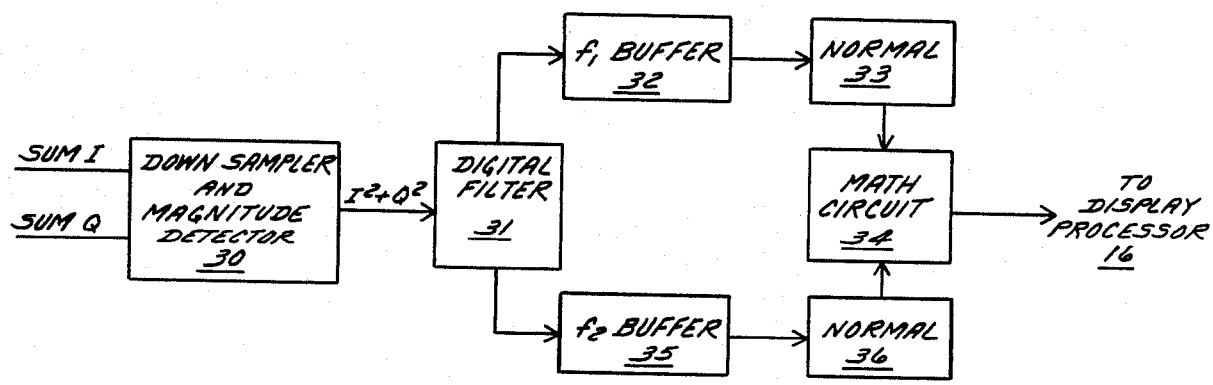
FIG. 4 is a block diagram showing the mid-processor of FIG. 1 in greater detail.

Turning now to FIG. 4, a preferred configuration of mid-processor 15 for implementing the improvements of the present invention is shown. The phase insensitive sum I and sum Q signals are provided from front-end processor 11 to down sampler and magnitude detector 30 which performs a reduction in samples through a rectangular window convolution. The down-sampled I and Q signals are preferably squared and then summed in down sampler and magnitude detector 30. The output of detector 30 is filtered by a digital filter 31 to narrow the bandwidth of the received intensity information. A buffer 32 receives filtered backscatter measurements corresponding to bursts having a fundamental frequency $f_1$. When a predetermined number of measurements (e.g., 3) have been stored in buffer 32, the measurements are normalized (i.e., averaged) in normalizing circuit 33. In the instance where measurements are taken at only one fundamental frequency, the averaged backscatter measurement from normalizing circuit 33 is passed through math circuit 34 unchanged to display processor 16. Information is then presented on display 17 either as an image, image overlay, or as an image histogram, as desired.

In the case where measurements are obtained at a plurality of fundamental frequencies in order to find frequency dependencies $W_1$ or $W_2$, measurements obtained at a second fundamental frequency $f_2$ are sent to a buffer 35. A plurality of $f_2$ measurements are averaged in normalizing circuit 26. The normalized estimates from normalizing circuit 33 and normalizing circuit 36 are then processed in math circuit 34. Math circuit 34 acts as a feature extractor employing weighting coefficients A to D as discussed above, which are determined by the fundamental frequencies and stored in a look-up table, for example.

In a particular implementation of the invention, it is possible to detect 4 dB shifts in mean backscatter levels between 1 cc target cells within a heart. The system achieves sufficient specificity and sensitivity by combining 10 independent samples per target cell. Intensity measurements are easily obtained at 5 mm intervals (either vector angle or depth). Using 3 separate burst lengths (equivalent to 2.5 independent measurements) at each backscatter pixel, it is easy to achieve the needed 10 samples within the 1 cc target volume. Uncertainty in the value obtained for mean backscatter cross section in the target cell is reduced to one-third of the uncertainty if only one sample was used. Thus, it is possible to separate tissue populations based on differential backscatter intensity.

The foregoing invention has provided a medical diagnostic modality having high sensitivity and specificity in detecting differential backscatter tissue populations. The use of a narrowband driving frequency or frequencies increases the volume of scatterers that contribute to a signal at each depth. The larger scattering volume produces better signal-to-noise measurements of the backscatter cross section in a target volume. By employing different interrogating burst lengths, partial independence of scatter estimates for a specific vector angle and depth are achieved. Sequential use of plural narrowband fundamental frequencies further improves the signal-to-noise performance and provides a means for separating tissue populations based on frequency dependence of the backscatter coefficient. The invention allows detection of localized variations in backscatter cross section per unit volume in an object, but is likewise applicable to detection of other intrinsic acoustic parameters by ultrasound.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed is:

1. An ultrasound apparatus for obtaining a two-dimensional backscatter image comprising:
   transducer means for transmitting ultrasound into and receiving ultrasound from an object to be studied, said transducer means having a fundamental frequency:
   pulse means coupled to said transducer means for driving said transducer means to emit narrowband ultrasonic waves, said waves having a bandwidth sufficiently narrow to obtain said image without range gating; and
   processing means coupled to said transducer means for calculating independent measurements of the backscatter intensity for a plurality of target areas in said object directly from echo waves received by said transducer means.

2. The apparatus of claim 1 wherein the 10 dB bandwidth of said narrowband waves is in the range of less than about 20 percent relative to said fundamental frequency.

3. The apparatus of claim 1 wherein said processing means is adapted to determine a backscatter intensity corresponding to each target area based on intensity measurements from a plurality of separate narrowband bursts, said bursts being driven by said pulse means and having a plurality of burst lengths.

4. The apparatus of claim 3 wherein the 10 dB bandwidth of each of said bursts is in the range of less than about 20 percent relative to said fundamental frequency.

5. The apparatus of claim 1 wherein said processing means is adapted to determine a backscatter intensity corresponding to each target area based on intensity measurements from a plurality of separate narrowband bursts, said bursts being driven by said pulse means and having a plurality of fundamental frequencies.

6. The apparatus of claim 5 wherein the 10 dB bandwidth of each of said bursts is in the range of less than about 20 percent relative to said fundamental frequency.

7. The apparatus of claim 1 wherein said processing means includes means for determining cyclic variations over time of said backscatter intensity for at least one of said target areas.

8. An ultrasound apparatus for measuring intrinsic acoustic parameters comprising:
   transducer means for transmitting ultrasound into and receiving ultrasound from an object to be studied;

pulser means coupled to said transducer means for driving said transducer means to emit ultrasonic bursts having variable lengths corresponding to predetermined numbers of cycles of the fundamental frequency of each respective burst; and processing means coupled to said transducer means for calculating ultrasound parameters for a plurality of target areas in said object, a respective parameter value corresponding to each target area being based on a plurality of measurements obtained from each target area with different burst lengths.

9. The apparatus of claim 8 wherein said pulser means drives said transducer means at a single fundamental frequency and wherein said processing means is adapted to calculate an average of said measurements.

10. A method for performing ultrasonic measurement of an object, comprising the steps of:
  insonifying said object with narrowband ultrasonic energy having a 10 dB bandwidth in the range of less than about 20 percent relative to the fundamental frequency of said ultrasonic energy;
  selecting a plurality of target volumes in said object for measurement; and
  detecting the backscatter intensity for each respective target volume.

11. The method of claim 10 wherein said detecting step includes interrogating each target volume with a plurality of bursts of different burst lengths.

12. The method of claim 10 wherein said detecting step includes interrogating each target volume with a plurality of bursts, each burst having a respective fundamental frequency, and wherein said backscatter intensity at each target volume is determined from intensity values from said plurality of bursts.

13. A method for ultrasonic examination of an object comprising the steps of:
  obtaining a backscatter intensity measurement N from a target area at a first fundamental frequency $f_1$;
  obtaining a backscatter intensity measurement N from said target area at a second fundamental frequency $f_2$;
  finding a solution for at least one of the factors $W_1$ and $W_2$ according to the equations $$W_1 = N(f_1)D - N(f_2)B \text{ and}$$

$$W_2 = N(f_2)A - N(f_1)C$$

where A, B, C, and D are predetermined constants; and
  assigning a factor value to said target area.

* * * * *